United States Patent [19]

Bornengo et al.

[11] 4,335,260

[45] Jun. 15, 1982

[54] PROCESS FOR THE PREPARATION OF N-DI-N-PROPYL-2,6-DINITRO-4-TRI-FLUOROMETHYLANILINE HAVING A LOW CONTENT OF NITROSAMINES

[75] Inventors: Mario Bornengo, Massa; Sergio Bacciarelli, Orzonovo, both of Italy

[73] Assignee: Montedison S.p.A., Milan, Italy

[21] Appl. No.: 263,508

[22] Filed: May 14, 1981

[30] Foreign Application Priority Data

May 15, 1980 [IT] Italy .................................. 22073 A/80

[51] Int. Cl.$^3$ .............................................. C07C 85/04
[52] U.S. Cl. ...................................... 564/406; 564/437
[58] Field of Search ................................ 564/406, 407

[56] References Cited

U.S. PATENT DOCUMENTS 1,401,631  12/1921  Moran .................................. 564/406

FOREIGN PATENT DOCUMENTS

| 869042 | 1/1979 | Belgium | 564/406 |
|---|---|---|---|
| 1057774 | 7/1979 | Canada | 564/406 |
| 1062729 | 9/1979 | Canada | 564/406 |
| 2161879 | 6/1973 | Fed. Rep. of Germany | 564/406 |
| 2816637 | 9/1978 | Fed. Rep. of Germany | 564/406 |

*Primary Examiner*—John Doll

[57] ABSTRACT

N-di-n-propyl-2,6-dinitro-4-trifluoromethylaniline ("Trifluralin") with a low content in nitrosamines (less than 1 ppm) is prepared by reacting 4-trifluoro-2,6-dinitro-chlorobenzene with di-n-propylamine under the following critical conditions:

feeding to the chlorobenzoderivative the di-n-propylamine containing an alkali metal hydroxide or an alkaline carbonate so that the pH value of the reaction mass is comprised between 7 and 7.5;

regulating the temperature of the reaction mass so that it does not exceed 70° C.; and operating in the presence of at least 50% by weight of water in the reaction mass.

1 Claim, No Drawings

PROCESS FOR THE PREPARATION OF N-DI-N-PROPYL-2,6-DINITRO-4-TRIFLUOROMETHYLANILINE HAVING A LOW CONTENT OF NITROSAMINES

BACKGROUND OF THE INVENTION

N-di-n-propyl-2,6-dinitro-4-trifluoromethyl-aniline is a herbicide marketed by Eli Lilly Co. under the commercial name of "Trifluralin", use thereof being described in U.S. Pat. No. 3,257,190.

According to said patent, "Trifluralin" may be prepared from 4-trifluoromethyl-2,6-dinitrochlorobenzene, by heating it with an excess of di-n-propylamine sufficient for blocking the hydrochloric acid that develops, di-n-propylamine hydrochloride being formed and removed by filtering and from which the n-propylamine may be recovered for recycling to the reaction with 4-trifluoromethyl-2,6-dinitrochlorobenzene.

Under such conditions, there are obtained, as by-products, considerable quantities of nitrosamines (which may attain up to 250 parts per million), which are considered dangerous for warm-blooded animals, and particularly for man, so much so that some laws put limits on the permissible concentration thereof in herbicides to be used on rural soils.

According to the Eli Lilly Co., Canadian Pat. No. 1,057,774, the nitrosamines present in the end-product may be considerably lowered if the "Trifluralin" is put into contact, in a liquid phase and at temperatures preferably below 120° C., with bromine, chlorine, N-bromosuccinimide, N-chlorosuccinimide, bromine chloride, pyridine perbromide or bromopyridine perbromide.

According to Canadian Pat. No. 1,062,729 one obtains the same result by treating the "Trifluralin" with $PCl_3$, $PCl_5$, $PBr_3$ or $POCl_3$, under the same conditions as in Canadian Pat. No. 1,057,774.

German Patent Appl. No. 2,816,637 discloses that the nitrosamines are removed from the "Trifluralin" by reaction thereof with an aldehyde or a ketone in the presence of HCl or HBr; while in Eli Lilly Belgian Pat. No. 869,042 the "Trifluralin" is treated with 20% HCl in ethanol at 90° C.

THE PRESENT INVENTION

One object of this invention is to provide a process for producing a "Trifluralin" that, as obtained, is practically free of nitrosamines.

Another object is to provide a simpler process for the synthesis of Trifluralin, in which the amount of the reaction by-products is lower.

These and other objects are achieved if, in accordance with the process of this invention, the reaction process between 4-trifluoromethyl-2,6-dinitro-chlorobenzene and di-n-propylamine, and contemporaneously with the amine, there is fed in an alkali metal hydroxide or an alkali carbonate in such quantities as to maintain the pH value constant at between 7 and 7.5, and the reaction is carried out at temperatures below 70° C. and in the presence of at least 50% of water in the reaction mass.

It appears that, under the conditions of the present process, the di-n-propylamine hydrochloride is not formed. In fact, in order for such hydrochloride to be formed, it would be necessary to lower the pH value to 4.3–4.5. The low temperature will hinder a loss of di-n-propylamine. All of these conditions result in an end product (Trifluralin) in which the nitrosamines content will reach, at most, 1 ppm.

The reaction forming the alkali chloride is exothermic and therefore must be kept under control by means of a suitable cooling system. The presence of water is, moreover, necessary for maintaining the sodium chloride present in solution and for its removal.

The quantities of nitrosamines found in the herbicide prepared according to the method of this invention, vary from 0.1 p.p.m. to 1 p.p.m. In order to achieve such results it is necessary to keep strictly to the indicated operating conditions; a drop in the pH value into the acid range can cause an increase of the nitrosamines to more than 1 p.p.m.; an increase of the temperature above 100° C. in an alkaline medium leads to losses of n-propylamine; an increase of the pH above 7.5 gives unsatisfactory yields because of the increase in secondary reactions.

The invention is illustrated by the following examples:

EXAMPLE 1

Into a 4 lt. flask were loaded 1,200 g of 4-trifluoromethyl-2,6-dinitro-chlorobenzene and 2 lts. of water, whereupon the temperature was brought up to 55° C., under stirring.

Through two drawing pipes were then contemporaneously additioned 450 g of 99% di-n-propylamine and 355 g of 40% b.w. NaOH; by means of a drawing electrode the flow was adjusted to maintain the pH constant between 7 and 7.5.

During the addition of the di-n-propylamine and NaOH, the flask was cooled by water so that the inside temperature did not exceed 55° C. On completion of the addition, the reaction mass was heated up to 70° C. for about 3 hours, while maintaining the pH at 7.2 (possibly adding a few drops of 40% b.w. NaOH).

The stirring and heating were then stopped and the organic phase (the lower phase) was allowed to mix through, after which the floating mother liquors were syphoned away. The mixture was then washed twice with 1 lt. of warm water (55%), each time under stirring, until neutrality was attained.

The molten product gradually coagulated. The yield in N-di-n-propyl-2,6-dinitro-4-trifluoromethylaniline was 97% b.w. calculated on the starting 4-trifluoromethyl-2,6-dinitro-chlorobenzene. The purity was 95%, while the nitrosamines present amounted to 0.1 ppm.

EXAMPLE 2 (Comparative)

Under the same operating conditions as those of Example 1, but adding the sodium hydroxide solution after having fed in all of the di-n-propylamine, the yield of end-product amounted to 95% b.w., but the quantity of nitrosamines present amounted to 250 ppm.

EXAMPLE 3 (Comparative)

Under the same conditions as those of Example 1, conducting the reaction by the contemporaneous addition of di-n-propylamine and sodium hydroxide solution, but allowing the temperature to rise spontaneously during the addition, the purity of the end-product obtained dropped to 92% while the nitrosamines contained therein amounted to 10 ppm.

EXAMPLE 4 (Comparative)

Under the same operating conditions as those of Example 1, 1,200 g of 4-trifluoromethyl-2,6-dinitro-chlorobenzene were loaded into the reactor, and heated up to 55° C. in the presence of 40% of water. Thereupon, the di-n-propylamine was added and, contemporaneously, the sodium hydroxide solution, maintaining the pH at a value between 7.2 and 7.5.

The content in nitrosamines in the end-product rose to 10 ppm, while the yield amounted to 95% b.w. and the product showed a purity of 94%.

We claim:

1. Process for producing herbicidal N-di-n-propyl-2,6-dinitro-4-trifluoromethylaniline containing nitrosamines in an amount lower than 1 ppm, characterized in that 4-trifluoromethyl-2,6-dinitro-chlorobenzene is reacted with di-n-propylamine in the presence of an alkali metal hydroxide or an alkali metal carbonate introduced contemporaneously with the di-n-propylamine so that the pH is maintained constant at a value comprised between 7 and 7.5; in that the temperature is regulated in such a way so as not to exceed 70° C.; and in that the reaction is carried out with at least 50% by weight of water present in the reaction mass.

* * * * *